(12) United States Patent
Knopff

(10) Patent No.: US 9,187,708 B2
(45) Date of Patent: Nov. 17, 2015

(54) ALDEHYDE AS PERFUMING INGREDIENT

(71) Applicant: FIRMENICH SA, Geneva (CH)

(72) Inventor: Oliver Knopff, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/367,218

(22) PCT Filed: Dec. 6, 2012

(86) PCT No.: PCT/EP2012/074703
§ 371 (c)(1),
(2) Date: Jun. 19, 2014

(87) PCT Pub. No.: WO2013/092240
PCT Pub. Date: Jun. 27, 2013

(65) Prior Publication Data
US 2015/0005213 A1    Jan. 1, 2015

(30) Foreign Application Priority Data
Dec. 20, 2011 (EP) .................................. 11194414

(51) Int. Cl.
| | | |
|---|---|---|
| *C11D 3/50* | (2006.01) |
| *C11B 9/00* | (2006.01) |
| *A61K 8/33* | (2006.01) |
| *A61Q 5/02* | (2006.01) |
| *A61Q 13/00* | (2006.01) |
| *A61Q 15/00* | (2006.01) |
| *A61Q 19/10* | (2006.01) |

(52) U.S. Cl.
CPC ................. *C11B 9/0015* (2013.01); *A61K 8/33* (2013.01); *A61Q 5/02* (2013.01); *A61Q 13/00* (2013.01); *A61Q 15/00* (2013.01); *A61Q 19/10* (2013.01); *C11D 3/50* (2013.01)

(58) Field of Classification Search
CPC ..................................................... C11B 9/0015
USPC ......................................................... 512/27
See application file for complete search history.

(56) References Cited

U.S. PATENT DOCUMENTS 3,872,172 A    3/1975 Bertele et al.
3,965,198 A * 6/1976 Bertele et al. ................. 568/840

FOREIGN PATENT DOCUMENTS

CH         491843    *  7/1970
JP    2008 308456 A   12/2008

OTHER PUBLICATIONS

International Search Report and Written Opinion, application PCT/EP2012/074703, mailed Jan. 2, 2013.

* cited by examiner

*Primary Examiner* — John Hardee
(74) *Attorney, Agent, or Firm* — Winston & Strawn LLP

(57) ABSTRACT

The present invention relates to the use as perfuming ingredient of -methyl-8- methylene-4, 9-decadienal, in particular to impart aldehydic notes evoking cardamon and/or floral notes evoking the lily of the valley.

9 Claims, No Drawings

ALDEHYDE AS PERFUMING INGREDIENT

TECHNICAL FIELD

The present invention relates to the field of perfumery. More particularly, it concerns the use as perfuming ingredient of 4-methyl-8-methylene-4,9-decadienal. Therefore, following what is mentioned herein, the present invention comprises also the invention's compound as part of a perfuming composition or of a perfuming consumer product.

PRIOR ART

4-Methyl-8-methylene-4,9-decadienal is a known product mentioned in various documents essentially as intermediate in the synthesis of beta-sinensal (a known component of orange oil) as for example in U.S. Pat. No. 3,872,172.

To the best of our knowledge, none of the documents citing the invention's compound reports or suggests any organoleptic properties of the compounds of formula (I), or any use of said compounds in the field of perfumery.

DESCRIPTION OF THE INVENTION

We have now surprisingly discovered that 4-methyl-8-methylene-4,9-decadienal, of formula

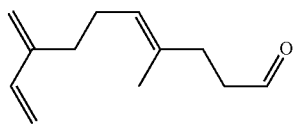

(I)

in the form of any one of its stereoisomers or a mixture thereof; can be used as perfuming ingredient, for instance to impart aldehydic notes, evoking cardamom, and/or floral notes evoking the lily of the valley.

For the sake of clarity, by the expression "any one of its stereoisomers", or the similar, it is meant the normal meaning understood by a person skilled in the art, i.e. that the invention's compound can be a pure diastereomer (e.g. the double bond is in a conformation E or Z).

According to a particular embodiment of the invention, said compound (I) is in the form of a mixture of diastereomer (4-E) and (4-Z) comprising at least 60%, or even 80% w/w, or even at least 90 or 95% w/w, of the (4-E) diastereomer.

As specific examples of the invention's compound, one may cite, as non-limiting example, (E)-4-methyl-8-methylene-4,9-decadienal which has a powerful odor characterized by a nice duality of aldehydic notes evoking cardamon and floral notes evoking the lily of the valley. The lily of the valley note reminds of the odor of Lilial® (3-(4-tert-butylphenyl)-2-methylpropanal from Givaudan S A, Vernier, Switzerland) and Cyclosal® (3-(4-isopropylphenyl)-2-methylpropanal), two well known perfuming ingredients. According to the specific use and the dosage of (E)-4-methyl-8-methylene-4,9-decadienal, said compound is able to display either one or the other type of notes and in particular it blends in a very harmonious manner with perfuming compositions of the to floral or green-aldehyde type.

When the odor of the invention's compounds is compared with that of the prior art compound beta-sinensal, then the invention's compounds distinguish themselves by a totally different odor since completely lacking of the typical citrus/orange odor of beta-sinensal.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified can be also ethanol, water/ethanol mixtures, limonene or other terpenes, isoparaffins such as those known under the trademark $Isopar$® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

According to a particular embodiment of the invention, particularly suitable perfuming bases are those having a herbaceous or green, floral, aldehyde, white flower and/or lily of the valley odor character. Indeed, when the invention's compound is admixed with a perfumery base having a herbaceous-aldehydic character, it confers/boosts/improves predominantly aldehyde/herbaceous notes. Similarly, when the invention's compound is admixed with a perfumery base having a lily of the valley character, said compound confers/boosts/improves predominantly the lily of the valley notes. In other words, although the pure compound displays a duality of odor, when admixed with perfumery base, according to the olfactive character of the latter, the invention's compound is able to confer /impart or boost only one dominant character.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modem perfumery, i.e. fine or functional perfumery, to positively impart or modify the odor of a consumer product into which said compound (I) is added. Consequently, a perfuming consumer product which comprises:
i) as perfuming ingredient, at least one compound of formula (I), as defined above; and
ii) a perfumery consumer base;
is also an object of the present invention.

The invention's compound can be added as such or as part of an invention's perfuming composition.

For the sake of clarity, it has to be mentioned that by "perfuming consumer product" it is meant a consumer product which is expected to deliver at least a perfuming effect, in other words it is a perfumed consumer product. For the sake of clarity, it has to be mentioned that by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient to upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.05% to 10% by weight, or even more, of the compounds of the invention based on the weight of the composition into which they are incorporated. Concentrations lower than these, such as in the order of 0.01% to 5% by weight, can be used when these compounds are incorporated into perfumed articles, percentage being relative to the weight of the article.

EXAMPLES

The invention will now be described in further detail by way of the following examples, wherein the abbreviations have the usual meaning in the art, the temperatures are indicated in degrees centigrade (° C.) ; the NMR spectral data were recorded in CDCl₃ (if not stated otherwise) with a 360 or 400 MHz machine for ¹H and ¹³C, the chemical shifts δ are indicated in ppm with respect to TMS as standard, the coupling constants J are expressed in Hz.

(E)-4-methyl-8-methylene-4,9-decadienal has been prepared according to the literature (see for example U.S. Pat. No. 3,872,172).

Example 1

Preparation of a Perfuming Composition

A perfuming composition for softener, of the herbaceous-floral-aldehyde type, was prepared by admixing the following ingredients:

| Parts by weight | Ingredient |
|---|---|
| 300 | Octyl acetate |
| 100 | Carbinol acetate |
| 50 | Cyclanol acetate |
| 180 | Terpenyl acetate |
| 600 | Verdyl acetate |
| 1000 | Isobornyl acetate |
| 10 | Aldehyde C 10 |
| 750 | Hexylcinnamic aldehyde |
| 70 | Aldehyde MNA |
| 10 | Aldehyde Supra |
| 50 | Allyl amyl glycolate |
| 20 | 10%* Ethyl caproate |
| 50 | Cetalox ®[1)] |
| 20 | Raspberry ketone |
| 20 | Ethyl cinnamate |
| 500 | Coranol ™[2)] |
| 20 | Delta Damascone |
| 200 | Dihydromyrcenol |
| 200 | 4-Cyclohexyl-2-methyl-2-butanol |
| 500 | (1-Ethoxyethoxy)cyclododecane |
| 400 | Florol ®[3)] |
| 450 | Hedione ®[4)] |
| 40 | 1,3-Benzodioxole-5-carbaldehyde |
| 50 | Hivernal ®[5)] |
| 500 | Iso E ®[6)] Super |
| 50 | Isoeugenol |
| 20 | 3,7-Dimethyl-2/3,6-nonadienenitrile |
| 100 | Lilyflore ®[7)] |
| 20 | 1-(2,2,3,6-Tetramethyl-cyclohexyl)-3-hexanol |
| 20 | Cristal moss |
| 20 | Myrrhone ®[8)] |
| 20 | 50%** (6R)-perhydro-3,6-dimethyl-benzo[b]furan-2-one |
| 50 | Neobutenone ®[9)] |
| 100 | Nirvanol ®[10)] |
| 30 | Trans-1-(2,2,6-trimethyl-1-cyclohexyl)-3-hexanol |
| 100 | 3-Methoxy-7,7-dimethyl-10-methylene-bicyclo[4.3.1]decane |
| 200 | Patchouli oil |
| 300 | Orange essential oil |
| 50 | 1-Methyl-4-(4-methyl-3-pentenyl)-3-cyclohexene-1-carbaldehyde |
| 400 | Verdyl propionate |
| 150 | Isobornyl propionate |
| 400 | Rose Wardia oil |
| 80 | Cis-3-Hexenyl salicylate |
| 100 | Salicynile ®[11)] |
| 900 | Sclareolate ®[12)] |
| 80 | Terpinolene |
| 50 | 2,4-Dimethyl-3-cyclohexen-1-carboxaldehyde |
| 50 | Gamma undecalactone |
| 20 | Vanilline |
| 300 | 2-Tert-butyl-1-cyclohexyl acetate |
| 9700 | |

*in dipropyleneglycol
**in isopropyle myristate
[1)]dodecahydro-3a,6,6,9a-tetramethyl-naphtho[2,1-b]furan; origin: Firmenich SA, Geneva, Switzerland
[2)]4-cyclohexyl-2-methyl-2-butanol; origin: Firmenich SA, Geneva, Switzerland
[3)]tetrahydro-2-isobutyl-4-methyl-4(2H)-pyranol; origin: Firmenich SA, Geneva, Switzerland
[4)]methyl dihydrojasmonate; origin: Firmenich SA, Geneva, Switzerland
[5)]3-(3,3/1,1-dimethyl-5-indanyl)propanal; origin: Firmenich SA, Geneva, Switzerland
[6)]1-(octahydro-2,3,8,8-tetramethyl-2-naphtalenyl)-1-ethanone; origin: International Flavors & Fragrances, USA
[7)](2,5-dimethyl-2,3-dihydro-1H-inden-2-yl)methanol; origin: Firmenich SA, Geneva, Switzerland
[8)]4-(2,2,C-3,T-6-tetramethyl-R-1-cyclohexyl)-3-buten-2-one; origin: Firmenich SA, Geneva, Switzerland
[9)]1-(5,5-dimethyl-1-cyclohexen-1-yl)-4-penten-1-one; origin: Firmenich SA, Geneva, Switzerland
[10)]3,3-dimethyl-5-(2,2,3-trimethyl-3-cyclopenten-1-yl)-4-penten-2-ol; origin: Firmenich SA, Geneva, Switzerland
[11)](2Z)-2-phenyl-2-hexenenitrile; origin: Firmenich SA, Geneva, Switzerland
[12)]propyl (S)-2-(1,1-dimethylpropoxy)propanoate; origin: Firmenich SA, Geneva, Switzerland The addition of 300 parts by weight of (E)-4-methyl-8-methylene-4,9-decadienal to the above-described composition reinforced the clean aldehyde aspect of the original composition by pushing the herbaceous aspect, and imparted also a twist of the cardamom type.

Example 2

Preparation of a Perfuming Composition

A perfuming composition for powder detergent, of the lily of the valley type, was prepared by admixing the following ingredients:

| Parts by weight | Ingredient |
|---|---|
| 60 | Cis-3-Hexenyl acetate |
| 200 | Cinnamic alcohol |
| 80 | 10%* Aldehyde C 10 |
| 60 | 10%* Aldehyde C 11 lenique |
| 80 | 10%* Aldehyde C 9 |
| 40 | Methyl anthranilate |
| 40 | Camomille Ester |
| 500 | Carbinol Muguet |
| 100 | Phenylethyl cinnamate |
| 1400 | Citronellol |
| 500 | Coranol ™[1)] |
| 40 | 2-Methyl-4-(2,2,3-trimethyl-3-cyclopenten-1-yl)-4-penten-1-ol |
| 200 | Geranium oil |
| 900 | Hedione ®[2)] |
| 400 | Hydroxycitronellal |
| 80 | 10%* Indol |
| 1200 | Jasmin oil |
| 500 | Lilyflore ®[3)] |
| 1000 | Linalol |
| 500 | Phenethylol |
| 440 | Phenylhexanol |
| 400 | Scentenal ®[4)] |
| 80 | (2,2-Dimethoxyethyl)benzene |
| 200 | Ylang oil |
| 9000 | |

*in dipropyleneglycol
**in isopropyle myristate
[1)]4-cyclohexyl-2-methyl-2-butanol; origin: Firmenich SA, Geneva, Switzerland
[2)]methyl dihydrojasmonate; origin: Firmenich SA, Geneva, Switzerland
[3)](2,5-dimethyl-2,3-dihydro-1H-inden-2-yl)methanol; origin: Firmenich SA, Geneva, Switzerland
[4)]8(9)-methoxy-tricyclo[5.2.1.0.(2,6)]decane-3(4)-carbaldehyde; origin: Firmenich SA, Geneva, Switzerland The addition of 1000 parts by weight of (E)-4-methyl-8-methylene-4,9-decadienal (10% dipropyleneglycol) into the above-described composition imparted to the latter a floral/lily of the valley effect very similar to the one obtained when, instead of the present aldehyde, was added the same amount of Lilial® (3-(4-tert-butylphenyl)-2-methylpropanal), a very well and widely used perfuming ingredient now strongly limited in use for regulatory reasons.

What is claimed is:

1. A method to confer, enhance, improve or modify the odor properties of a perfuming composition or of a perfumed article, which method comprises adding to said composition or article an effective amount of 4-methyl-8-methylene-4,9-decadienal in the form of any one of its stereoisomers or a mixture thereof.

2. Method according to claim 1, wherein 4-methyl-8-methylene-4,9-decadienal is used in the form of a mixture of diastereomer (4-E) and (4-Z) comprising at least 80% w/w of the (4-E) diastereomer.

3. Method according to claim 1, wherein it is used (E)-4-methyl-8-methylene-4,9-decadienal.

4. Method according to claim 1, wherein 4-methyl-8-methylene-4,9-decadienal is added to impart aldehydic notes and/or lily of the valley.

5. A perfuming composition comprising
   i) 4-methyl-8-methylene-4,9-decadienal in the form of any one of its stereoisomers or a mixture thereof;
   ii) at least one ingredient selected from the group consisting of a perfumery carrier and a perfumery base; and
   iii) optionally at least one perfumery adjuvant.

6. A perfuming composition according to claim 5, wherein said perfumery base has a herbaceous-aldehydic or an lily of the valley character.

7. A perfuming consumer product comprising:
   i) 4-methyl-8-methylene-4,9-decadienal in the form of any one of its stereoisomers or a mixture thereof; and
   ii) a perfumery consumer base.

8. A perfuming consumer product according to claim 7, wherein the perfumery consumer base is a perfume, a fabric care product, a body-care product, an air care product or a home care product.

9. A perfuming consumer product according to claim 7, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *

UNITED STATES PATENT AND TRADEMARK OFFICE
CERTIFICATE OF CORRECTION

PATENT NO. : 9,187,708 B2  
APPLICATION NO. : 14/367218  
DATED : November 17, 2015  
INVENTOR(S) : Knopff Page 1 of 1

It is certified that error appears in the above-identified patent and that said Letters Patent is hereby corrected as shown below:

<u>Title Page:</u>
Item (57) ABSTRACT, line 2, delete "-methyl-8-" and insert -- 4-methyl-8- --.

Signed and Sealed this
First Day of March, 2016

Michelle K. Lee
*Director of the United States Patent and Trademark Office*